United States Patent [19]
Sakaue et al.

[11] Patent Number: 5,739,538
[45] Date of Patent: Apr. 14, 1998

[54] PNEUMATIC INFRARED GAS DETECTOR

[75] Inventors: Satoru Sakaue; Mutsumi Nagumo; Michihiko Tsuruoka, all of Tokyo, Japan

[73] Assignee: Fuji Electric Co., Ltd., Japan

[21] Appl. No.: 689,073

[22] Filed: Jul. 30, 1996

[30] Foreign Application Priority Data

Jul. 31, 1995 [JP] Japan .................... 7-195272

[51] Int. Cl.⁶ .................................... G01N 21/61
[52] U.S. Cl. .............. 250/345; 250/339.13; 250/344
[58] Field of Search ........................... 250/345, 344, 250/339.13

[56] References Cited

U.S. PATENT DOCUMENTS

| | | | |
|---|---|---|---|
| 3,725,702 | 4/1973 | Schaefer | 250/343 |
| 3,770,974 | 11/1973 | Fertig | 250/344 |
| 3,968,369 | 7/1976 | Luft | 250/344 |
| 4,598,201 | 7/1986 | Fertig et al. | 250/343 |

FOREIGN PATENT DOCUMENTS

| | | |
|---|---|---|
| 51-144682 | 12/1976 | Japan . |
| 53-38941 | 10/1978 | Japan . |
| 56-122937 | 9/1981 | Japan . |
| 61-47540 | 3/1986 | Japan . |

*Primary Examiner*—Constantine Hannaher
*Attorney, Agent, or Firm*—Rossi & Associates

[57] ABSTRACT

A pneumatic infrared gas detector includes a pair of expansion chambers and a pair of pressure chambers, each of which is connected at one end thereof to the corresponding expansion chamber. Each of the pressure chambers is divided by a diaphragm into a first chamber connected to a corresponding expansion chamber, and a second chamber, such that the first chamber of one of the pair of pressure chambers is connected to the second chamber of the other of the pressure chambers through a first communication path, and such that the second chamber of the above-indicated one of the pressure chambers is connected to the first chamber of the other of the pressure chambers through a second communication path. A pair of pneumatic pressure detecting elements are provided each of which includes an electret film having one surface on which an electrode is formed, and an electrode plate disposed in opposed relationship with the electret film. The electret film is formed on a first side of a corresponding one of the diaphragms in each pressure chamber, and the electrode plate is supported and fixed at a position that is opposed to a second side of the corresponding diaphragm.

7 Claims, 7 Drawing Sheets

PNEUMATIC INFRARED GAS DETECTOR

FIELD OF THE INVENTION

The present invention relates to an infrared gas analyzer employing a pneumatic detector, for qualitatively and quantitatively analyzing respective components contained in a measurement gas. In particular, this invention is concerned with improvement in a detector portion of the infrared gas analyzer.

BACKGROUND OF THE INVENTION

A known example of an infrared gas analyzer employing a pneumatic detector is shown in FIG. 7 as including a motor 43, a rotary chopper 44, an infrared light source 45, a beam divider cell 46, light-transmitting windows 47–52, a measurement cell 53, a reference cell 54, an inlet tube 55, an outlet or discharge tube 56, an infrared gas detector 6, and expansion chambers 7a, 7b.

In operation, the reference cell 54 and the measurement cell 53 are intermittently irradiated with infrared rays emitted by the infrared light source 45, through the rotary chopper 44, beam divider cell 46, light-transmitting windows 47, 49 and others. The infrared gas detector 6 converts a degree of absorption of the infrared rays transmitted through a reference gas contained in the reference cell 54, and a degree of absorption of the infrared rays transmitted through a measurement gas contained in the measurement cell 53, to corresponding levels of pressure, which are detected as variations in the electrostatic capacity.

With regard to the infrared gas detector as described above, there are known techniques for removing vibrational noises, as disclosed in Japanese Patent No. 53-38941 or as shown in FIG. 8, for example. Referring to FIG. 8, a main detector 1 and an auxiliary detector 2 are installed independently of each other, and variations in the pressure in the main detector 1 are detected as variations in the electrostatic capacity. The vibration noises are removed by electrically calculating signals produced by the main detector 1 and the auxiliary detector 2.

To remove electric noises, there are known techniques as disclosed in Japanese laid-open Patent Publication No. 51-144682 or as shown in FIG. 9. This figure shows a dual fixed pole type differential detector in which two fixed poles 4, 5 are provided with one movable pole 3 interposed therebetween, so as to increase amounts of signals to be produced.

If the vibrational noises are to be removed by electrically calculating the signals from the main and auxiliary detectors 1, 2, as in the known example of Japanese Patent No. 53-38941, an electric system tends to be complicated, and a difference may arise in the forms of vibrations between the two detectors 1, 2 which are located in spaced-apart relationship with each other. This may result in insufficient removal of vibrational noises in a micro-vibration range, for example.

If the detection is carried out by a differential method using the two fixed poles, as in the known example of Japanese laid-open Patent Publication No. 51-144682, the vibrational noises may undesirably increase as the amounts of signals increase.

It is therefore an object of the present invention to provide a pneumatic infrared gas detector which is able to suppress or prevent noises, assuring an improved signal to noise ratio (S/N).

SUMMARY OF THE INVENTION

The above object may be accomplished according to one aspect of the present invention, which provides a pneumatic infrared gas detector comprising: first and second expansion chambers; first and second pressure chambers, each of which is connected at one end thereof to a corresponding one of the first and second expansion chambers; first and second diaphragms, respectively located in the first and second pressure chambers, for dividing each of the first and second pressure chambers into a first chamber connected to a corresponding one of the first and second expansion chambers and a second chamber, wherein the first chamber of the first pressure chamber is connected to the second chamber of the second pressure chamber through a first communication path, and wherein the second chamber of the first pressure chamber is connected to the first chamber of the second pressure chamber through a second communication path; and first and second pneumatic pressure detecting elements, respectively located in the first and second pressure chambers, each of the first and second pneumatic pressure detecting elements comprising an electret film having one surface on which an electrode is formed and an electrode plate disposed in opposed relationship with the electret film, wherein the electret film is formed on a first side of a corresponding one of the first and second diaphragms in each of the first and second pressure chambers and the electrode plate is supported and fixed at a position that is opposed to a second side of the corresponding one of the first and second diaphragms.

In the pneumatic infrared gas detector constructed as described above, a detected pressure received from each of the pair of expansion chambers is transmitted to one side of one of the pair of pressure chambers and the opposite side of the other pressure chamber, through a corresponding one of mutually crossing communication paths, so that the diaphragm in one of the pressure chambers is deformed in the direction opposite to that in which the diaphragm in the other pressure chamber is deformed, depending upon a difference between the detected pressures from the expansion chambers. As a result, a voltage is generated between the electret film and the electrode plate opposed to the electret film, so as to provide a signal component while canceling vibrational noises, assuring improved detecting accuracy. Accordingly, the present infrared gas detector is able to detect a measurement gas in a relatively low density range with sufficiently high accuracy.

The above-indicated first and second pressure chambers are disposed in parallel with each other on the same plane, and a single electret film, retained at opposite surface thereof, forms the first and second diaphragms in the first and second pressure chambers. In this arrangement, a detected pressure received from each of the pair of expansion chambers is transmitted to one side of one of the pair of pressure chambers and the opposite side of the other pressure chamber, through a corresponding one of mutually crossing communication paths, so that the diaphragm in one of the pressure chambers is deformed in the direction opposite to that in which the diaphragm in the other pressure chamber is deformed, depending upon a difference between the detected pressures from the expansion chambers. As a result, a voltage is generated between the electret film forming the diaphragm and the electrode plate opposed to the electret film, so as to provide a signal component with improved sensitivity while canceling vibrational noises. Since the pressure chambers are provided in parallel with each other on the same plane, and the diaphragms for dividing the pressure chambers are formed from a continuous single electret film, the pair of pressure chambers and the pressure detecting elements exhibit the same operating characteristics, assuring further improved detecting accuracy. Consequently, variations in detecting characteristics are reduced, thus making it possible to measure a low-density gas with sufficiently high detecting accuracy.

The same object may be accomplished according to another aspect of the present invention, which provides a pneumatic infrared gas detector comprising: a pair of expansion chambers; an upper pressure chamber and a lower pressure chamber connected to one of the pair of expansion chambers; an intermediate pressure chamber formed between the upper pressure chamber and the lower pressure chamber, through upper and lower diaphragms, the intermediate pressure chamber being connected to the other of the pair of expansion chambers; and an upper and a lower pneumatic pressure detecting element corresponding to the upper and lower diaphragms, each of which comprises an electret film having one surface on which an electrode is formed, and an electrode plate disposed in opposed relationship with the electret film, wherein the electret film of each of the upper and lower pneumatic pressure detecting elements is formed on a first side of a corresponding one of the upper and lower diaphragms and the electrode plate of each of the upper and lower pneumatic pressure detecting elements is supported and fixed at a position that is opposed to a second side of the corresponding one of the first and second diaphragms.

In the pneumatic infrared gas detector constructed as described above, a detected pressure received from one of the pair of expansion chambers is transmitted to the upper and lower pressure chambers, while a detected pressure received from the other expansion chamber is transmitted to an intermediate pressure chamber, so that the diaphragms in these pressure chambers are deformed in the opposite directions depending upon a difference between the detected pressures. As a result, a voltage is generated between the electret film and the electrode plate opposed to the electret film, so that both of the pneumatic pressure detecting elements output pressure signals based on the voltage thus generated. The pressure signal thus generated is electrically processed so as to cancel noises, such as external vibrations, whereby only normal variations in the pressure can be detected with high efficiency. Consequently, the pneumatic infrared gas detector is able to effect measurements with respect to a low-density gas with high accuracy. Further, the present infrared gas detector, in which the pressure chambers are superposed on each other, can be advantageously made compact or small-sized.

The same object may be accomplished according to a further aspect of the present invention, which provides a pneumatic infrared gas detector comprising: a pair of expansion chambers; upper pressure chamber and lower pressure chamber connected to one of the pair of expansion chambers; an intermediate pressure chamber formed between the upper pressure chamber and the lower pressure chamber, through respective upper and lower diaphragms, the intermediate pressure chamber being connected to the other of the pair of expansion chambers; and upper and lower pneumatic pressure detecting elements, each including an electret film having one surface on which an electrode is formed, the electret films of the upper and lower pneumatic pressure detecting elements being charged to have different polarities; wherein the upper and lower diaphragms respectively comprise the electret film of the upper and lower pressure detecting elements, which are positioned such that charged surfaces of the electret films of the upper and lower pressure detecting elements are opposed to each other.

In the pneumatic infrared gas detector constructed as described above, a detected pressure received from one of the pair of expansion chambers is transmitted to the upper and lower pressure chambers, while a detected pressure received from the other expansion chamber is transmitted to the intermediate pressure chamber, so that the diaphragms in these pressure chambers are deformed in the opposite directions depending upon a difference in the detected pressures. As a result, a voltage is generated between the two electret films which form the diaphragms, so that both of the pneumatic pressure detecting elements output pressure signals based on the voltage thus generated. Thus, the pneumatic infrared gas detector is able to measure a low-density gas with high accuracy. Further, a fixed electrode plate needs not be provided if the electret films having electrodes formed on one side thereof are charged with mutually different polarities.

BRIEF DESCRIPTION OF THE DRAWINGS

The invention will be described in greater detail with reference to certain preferred embodiments thereof and the accompanying drawings, wherein.

DETAILED DESCRIPTION OF THE PREFERRED EMBODIMENTS

Figure 1:
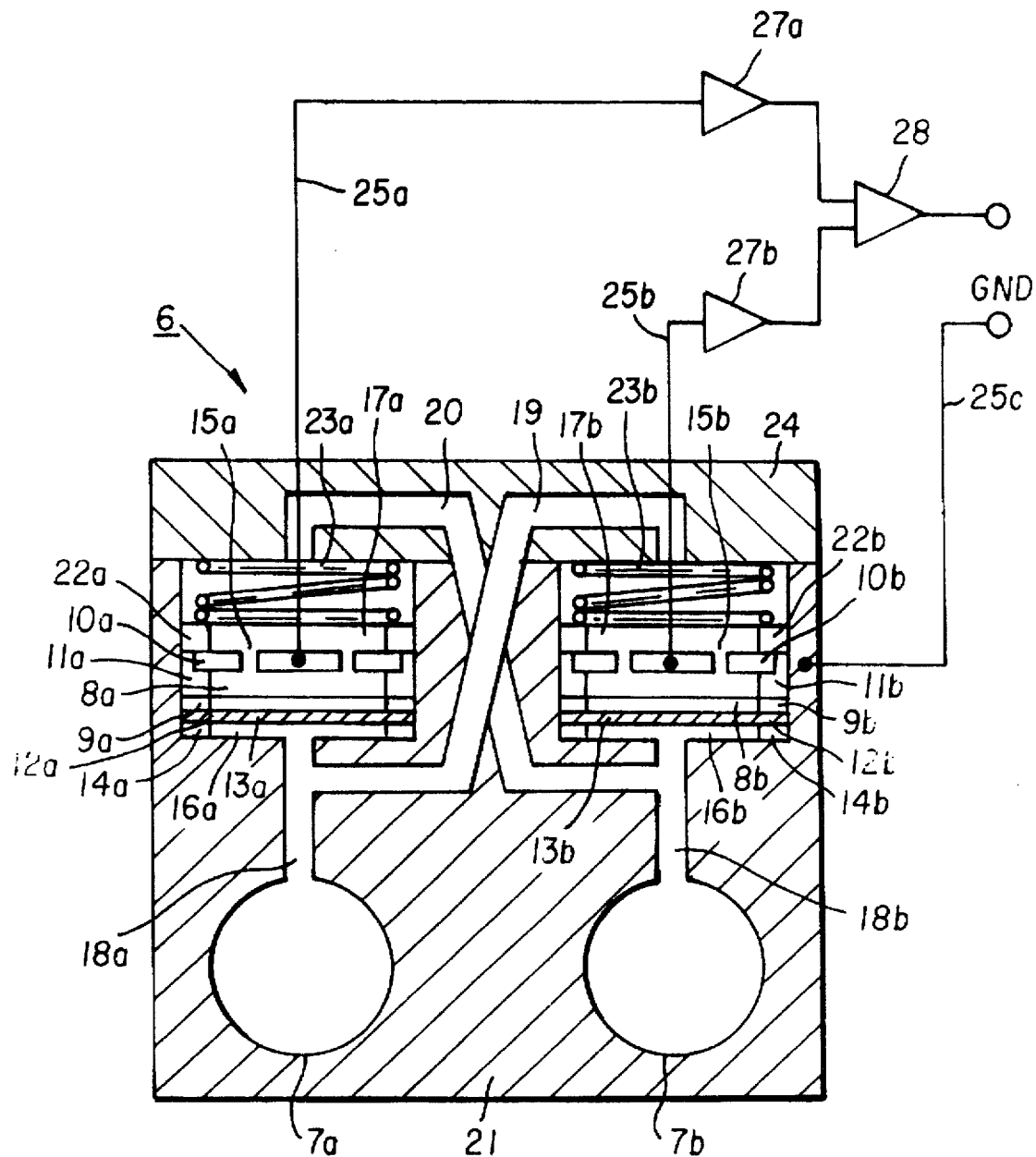
FIG. 1 is a view showing the structure of the first embodiment of the present invention.

Referring to FIG. 1, which illustrates a first embodiment of the present invention, an infrared gas detector 6 is provided with a first pneumatic pressure detecting element 8a and a second pneumatic pressure detecting element 8b. These detecting elements 8a, 8b include respective diaphragms 9a, 9b that consist of electret films, and respective back plates 10a, 10b serving as electrode plates. Insulating spacers 11a, 11b having a low dielectric constant and a thickness of several dozens of microns are interposed between the corresponding diaphragms 9a, 9b and back plates 10a, 10b, such that the back plate 10a (10b), spacer 11a (11b) and diaphragm 9a (9b) are superposed on each other in the order of description.

To produce each of the diaphragms 9a, 9b, an electrode 12a, 12b is formed by sputtering, for example, over the entire area of one surface of a non-polar polymeric material, such as FEP teflon, and a film surface of the electrode is positively or negatively charged by corona discharge, for example, to thus provide an electret film 13a, 13b. The electrodes 12a, 12b of the electret films 13a, 13b are respectively bonded to conductive frames 14a, 14b having a cylindrical shape, such that the electrodes 12a, 12b are held in electrical continuity with the frames 14a, 14b, and such that uniform tensile force is applied to the electret films 13a, 13b in the radial direction.

The back plates 10a, 10b are formed with respective openings 15a, 15b that permit free passage of the gas contained in the infrared gas detector 6, and cooperate with the electrodes 12a, 12b to form capacitance (electrostatic capacity) therebetween. Pressure chambers 16a, 16b are formed on the side of the lower surfaces of the diaphragms 9a, 9b, respectively, and pressure chambers 17a, 17b are formed on the side of the upper surfaces of the diaphragms 9a, 9b, respectively, such that the back plates 10a, 10b are disposed within the chambers 17a, 17b. The pressure chamber 16a communicates with the pressure chamber 17b, through the expansion chamber 7a and communication path 19, while the pressure chamber 16b communicates with the pressure chamber 17a, through the expansion chamber 7b and communication path 20.

The conductive frames 14a, 14b abutting on a first conductive housing 21 are electrically connected to the electrodes 12a, 12b and a lead wire 25c that is connected to the ground.(GND). To insulate the back plates 10a, 10b from the first housing 21, spacers 22a, 22b made of an insulating material are inserted from above to rest on the back plates 10a, 10b and spacers 11a, 11b. These spacers 22a, 22b are pressed downward and supported by a lid 24, through respective springs 23a, 23b. The lid 24 is fixed to the first housing 21 by means of screws or the like (not shown). The back plates 10a, 10b of the thus constructed infrared gas detector 6 are connected to impedance converting elements 27a, 27b, by means of lead wires 25a, 25b, respectively. These converting elements 27a, 27b are connected to a differential amplifier 28.

There will be explained in detail the operation of the infrared gas detector 6 constructed as described above.

Measurement rays of light and reference rays of light that are incident upon the expansion chambers 7a, 7b are absorbed in the respective expansion chambers 7a, 7b, with a result of variations in the pressure of the chambers 7a, 7b. If the pressure of the expansion chamber 7a increases to be higher than that of the expansion chamber 7b, for example, the pressure chambers 16a, 17b have higher levels of pressure than the pressure chambers 16b, 17a, whereby the diaphragm 9a is deformed upward and the diaphragm 9b is deformed downward. As a result, a spacing between the electrode 12a and the back plate 10a is decreased, and a spacing between the electrode 12b and the back plate 10b is increased. If both of the electrodes 12a, 12b consisting of the electret films 13 are positively charged, therefore, a negative (−) voltage is generated by the detecting element 8b, and a positive (+) voltage is generated by the detecting element 8a.

If external vibrations are applied to the infrared gas detector 6, to accelerate the detector 6 downward, for example, both of the diaphragms 9a, 9b undergo upward displacement, whereby the detecting elements 8a, 8b both produce positive (+) voltages. These outputs of the detecting elements 8a, 8b are subjected to impedance conversion by the converting elements 27a, 27b, and received by the differential amplifier 28. The differential amplifier 28 calculates a different between these outputs, so as to amplify normal signals and cancel noises due to the external vibrations, thereby to provide its outputs with high S/N ratios.

Figure 2:
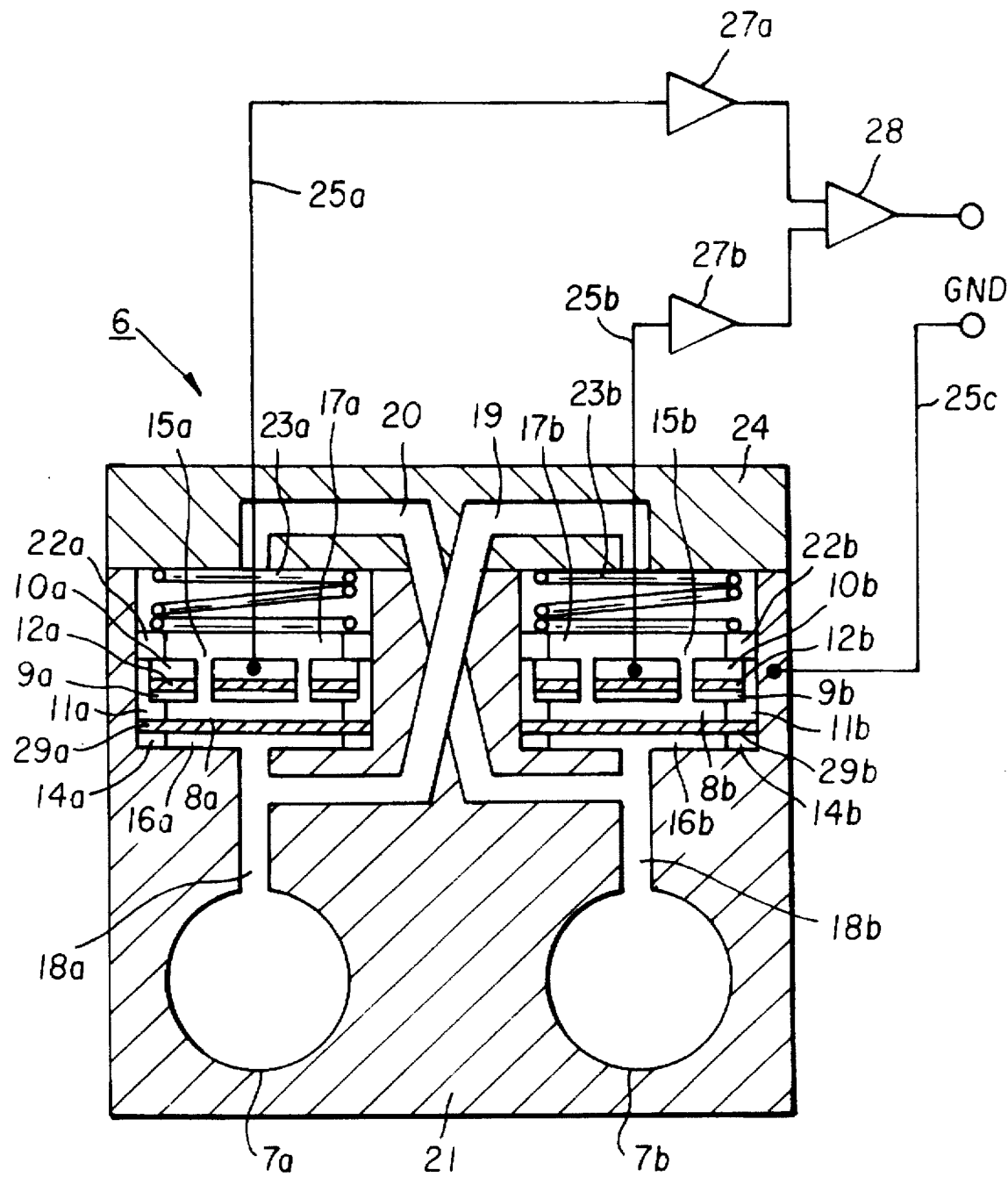
FIG. 2 is a view showing a modified example of the embodiment of FIG. 1.

FIG. 2 is a modified example of the embodiment of FIG. 1. The same reference numerals as used in FIG. 1 are used in FIG. 2 to identify corresponding elements.

The modified example is different from the first embodiment of FIG. 1 in that the back plates 10a, 10b are formed by the electret films and electrodes 12a, 12b, and diaphragms 29a, 29b are provided so as to face the respective back plates 10a, 10b. Each of the diaphragms 29a, 29b consists of a thin metal film, or a plastic film having an electrode formed on one surface thereof, and is electrically connected to the lead wire 25c, through a corresponding one of the frames 14a, 14b and the first housing 21. In this arrangement, the diaphragm may be formed of a material, such as FEP teflon, which does not have an electret property. If a low-density material is used for forming the diaphragms, the influence of external vibrations on the acceleration of the diaphragms is reduced, assuring even higher measurement accuracy. The other structure of this example is similar to that of the embodiment of FIG. 1, and therefore will not be described in detail.

Figure 3:
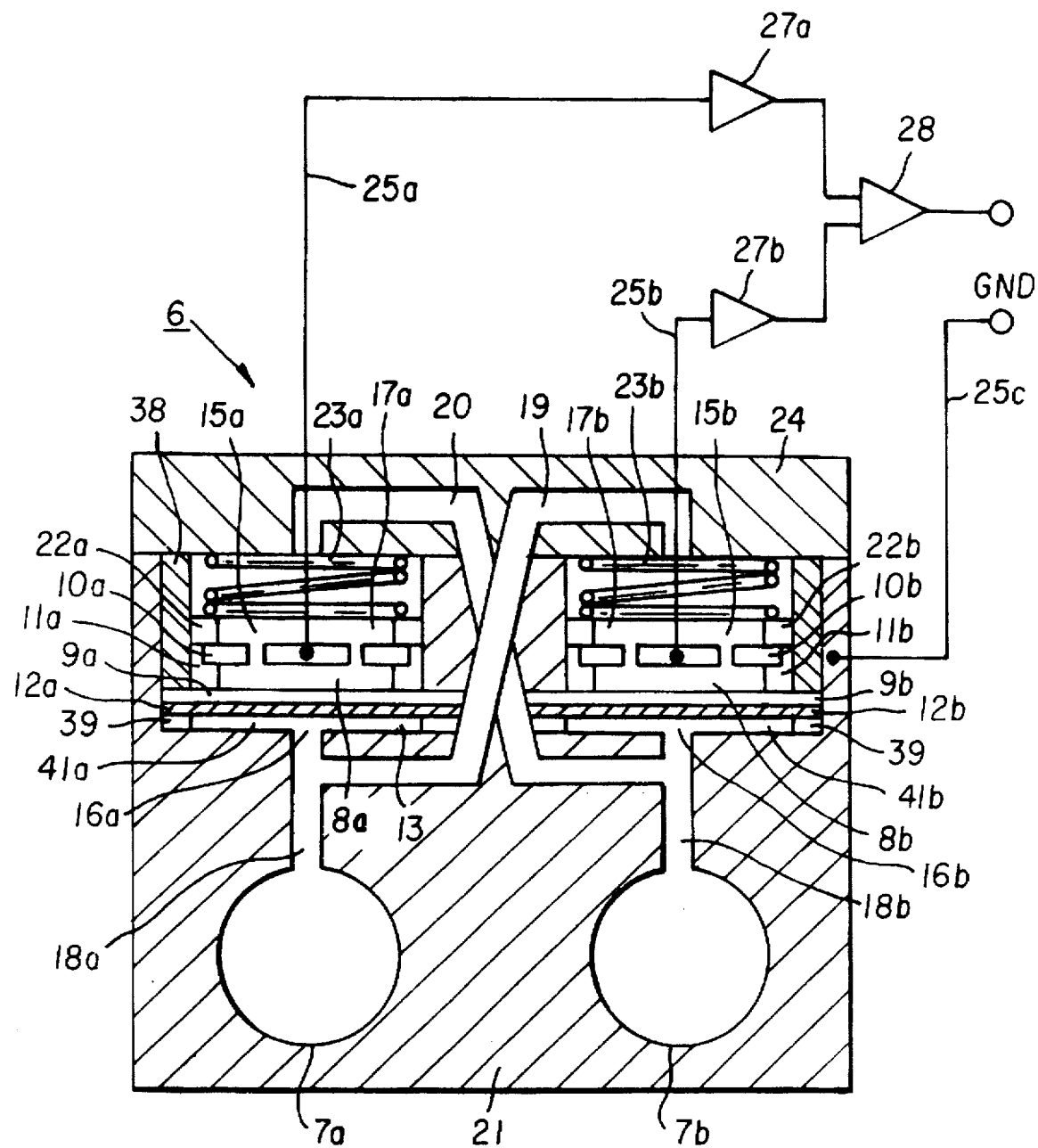
FIG. 3 is a view showing the structure of the second embodiment of the present invention.

FIG. 3 is a view showing the second embodiment of the present invention. This embodiment is different from those of FIGS. 1 and 2 in that a single electret film 13 having one surface on which the electrodes 12 are formed and the other surface that is electrically charged is mounted on the first housing 21, through a conductive frame 39 formed with two circular apertures 41a, 41b. The differences will be explained in greater detail.

The electrodes 12a, 12b of FIG. 3 are both fixed in position with uniform tensile force applied thereto in the radial direction. The electrodes 12a, 12b are also fixed at their charged surfaces by a second housing 38 formed with apertures having the same shape as those of the frame 39. Further, insulating spacers 11a, 11b, back plates 10a, 10b serving as electrode plates, and spacers 22a, 22b are inserted in the apertures of the second housing 38 in the order of description, and are pressed downward and supported by the lid 24, through the respective springs 23a, 23b. In this manner, the first pneumatic pressure detecting element 8a and the second pneumatic pressure detecting element 8b are formed.

With the detecting elements 8a, 8b thus constructed, the two diaphragms 9a, 9b are always subjected to same tensile force when the tensile force is applied to the electret film 13 for attachment to the frame 39. Therefore, the diaphragms 9a, 9b exhibit the same displacement characteristics with respect to the pressure, and both of the detecting element 8a, 8b may be manufactured under the same conditions in terms of the surface charge and charge-injection depth of the electret film 13, for example. Consequently, variations in characteristics between the two detecting elements 8a, 8b are extremely small, and noise voltage is far less likely to be generated when external vibrations are applied to the detecting elements. With the noises thus reduced, the measurement range can be expanded to include a relatively low-density range. Further, there is no need for electrical adjustment for equalizing voltages generated at two separate films.

Figure 4:
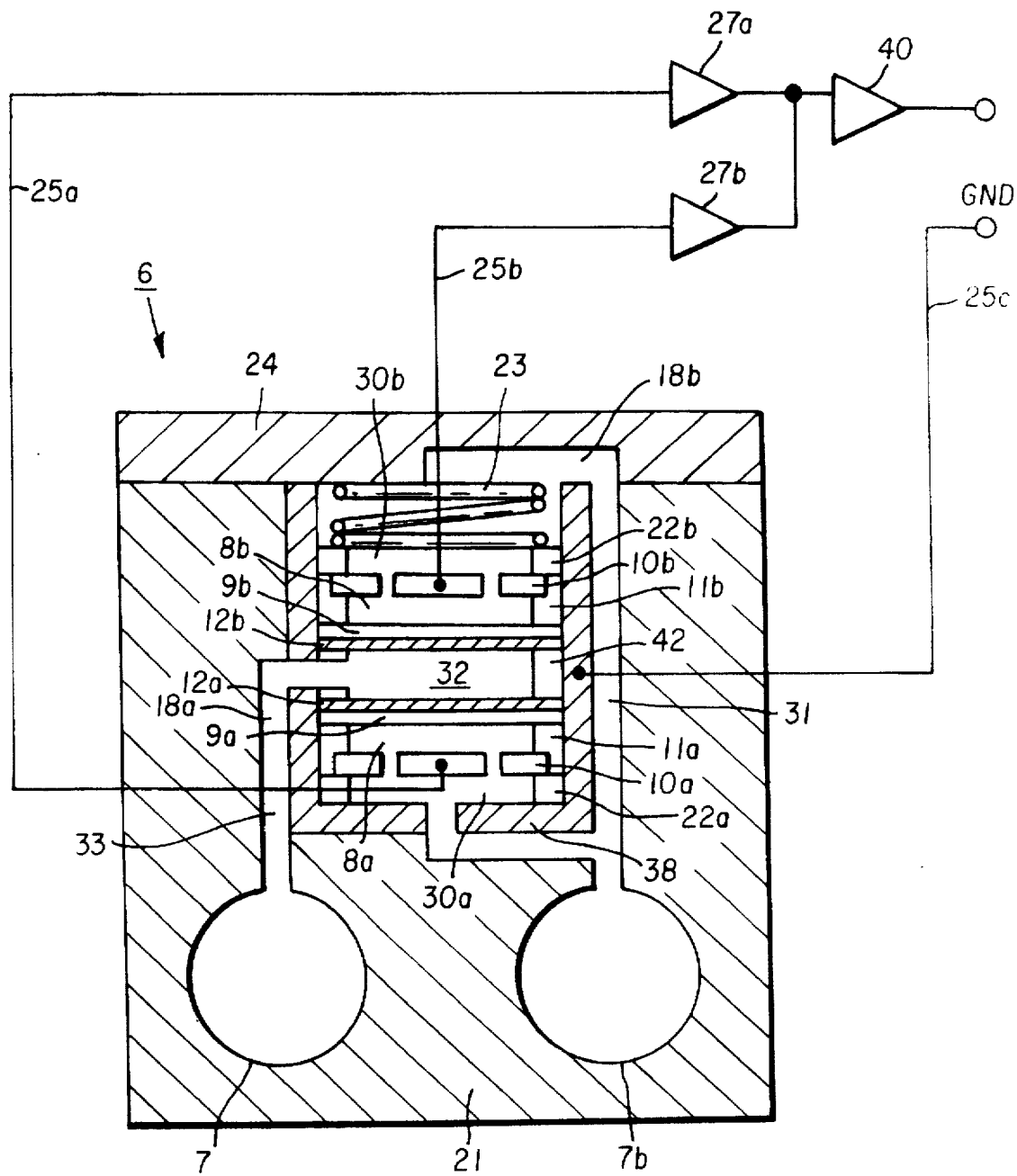
FIG. 4 is a view showing the structure of the third embodiment of the present invention.

FIG. 4 is a view showing the third embodiment of the present invention. This embodiment is different from those of FIG. 1 through FIG. 3 in that the first pneumatic pressure detecting element 8a and the second pneumatic pressure detecting element 8b are superposed on each other in the direction of the thickness thereof, with a conductive spacer 42 interposed between the two elements 8a, 8b. The differences will be hereinafter explained in greater detail.

The pressure chambers 30a, 30b are formed on the sides of the respective back plates 10a, 10b, with respect to the diaphragms 9a, 9b, such that the pressure chambers 30a, 30b communicate with each other through a communication path 31, and are also connected to a connecting path 18b. Intermediate pressure chamber 32 is formed between the diaphragm 9a and diaphragm 9b which consist of electret films, such that the pressure chamber 32 is connected to the connecting path 18a through a communication path 33. The diaphragm 9a, 9b, insulating spacer 11a, 11b having a thickness of several dozens of microns, back plate 10a, 10b, and spacer 22a, 22b having a low dielectric constant are superposed on each other in the order of description, and supported within the conductive second housing 38 having a cylindrical shape. The electrodes 12a, 12b of the diaphragms 9a, 9b are electrically connected to the second housing 38, through the conductive spacer 42 held in abutting contact with the electrodes 12a, 12b, and the second housing 38 is connected to the lead wire 25c which is connected to the ground (GND).

Figure 5:
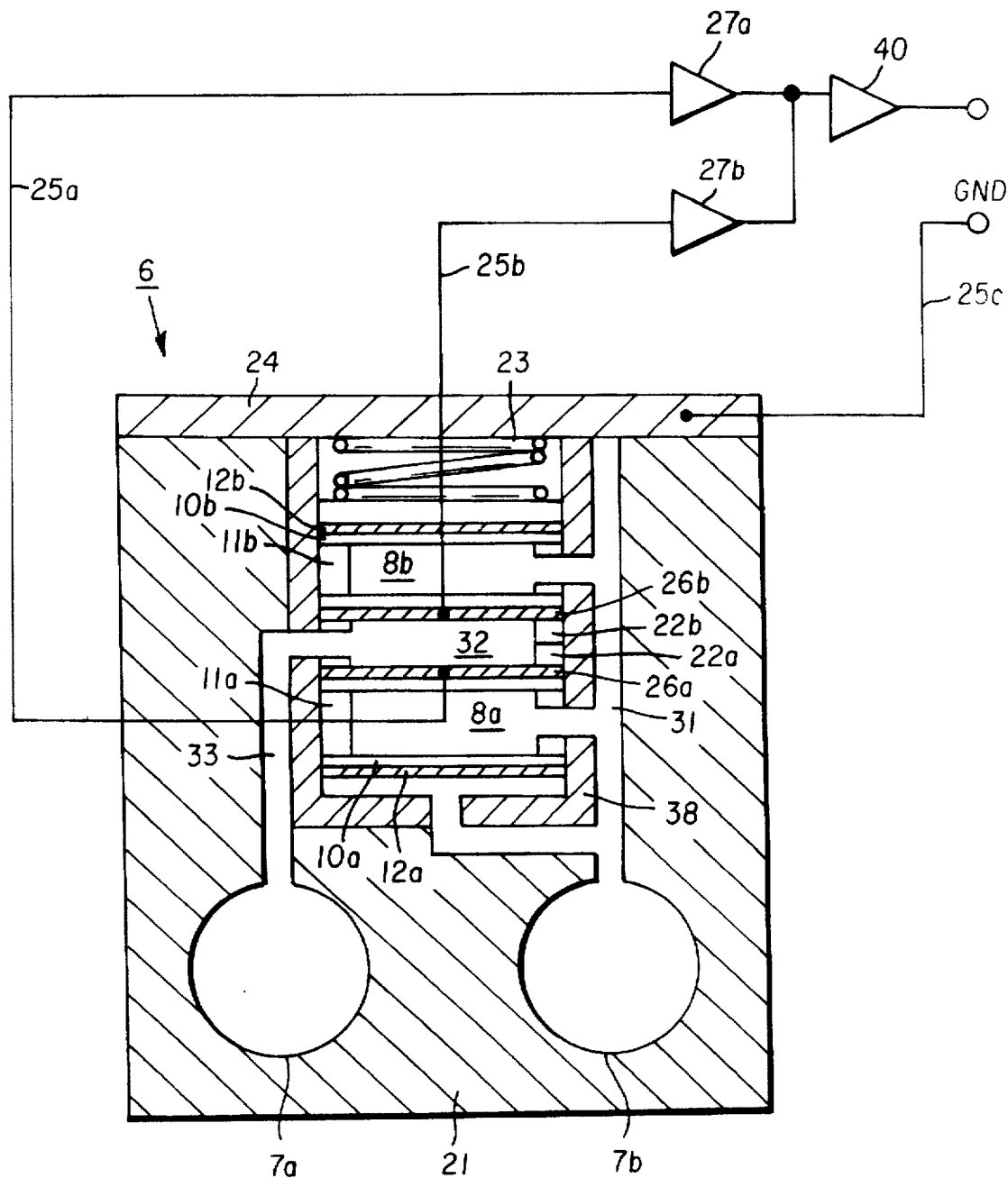
FIG. 5 is a view showing a modified example of the embodiment of FIG. 4.

FIG. 5 is a modified example of the third embodiment of FIG. 4. This example is different from the embodiment of FIG. 4 in that the back plates 10a, 10b are respectively formed from electret films on which the electrodes 12a, 12b are formed, and diaphragms 26a, 26b are disposed in opposed relationship with the back plates 10a, 10b. Each of these diaphragms 26a, 26b consists of a thin metal film or a plastic film having one surface on which an electrode is formed. Thus, the diaphragm may be formed of a material, such as FEP teflon, which does not have an electret property. While both of the electret films are either positively or negatively charged in the embodiment of FIG. 4, the charge on one of the electret films may be different from the charge on the other electret film. In this case, a difference in the voltage between the two detecting elements 8a, 8b is calculated.

Figure 6:
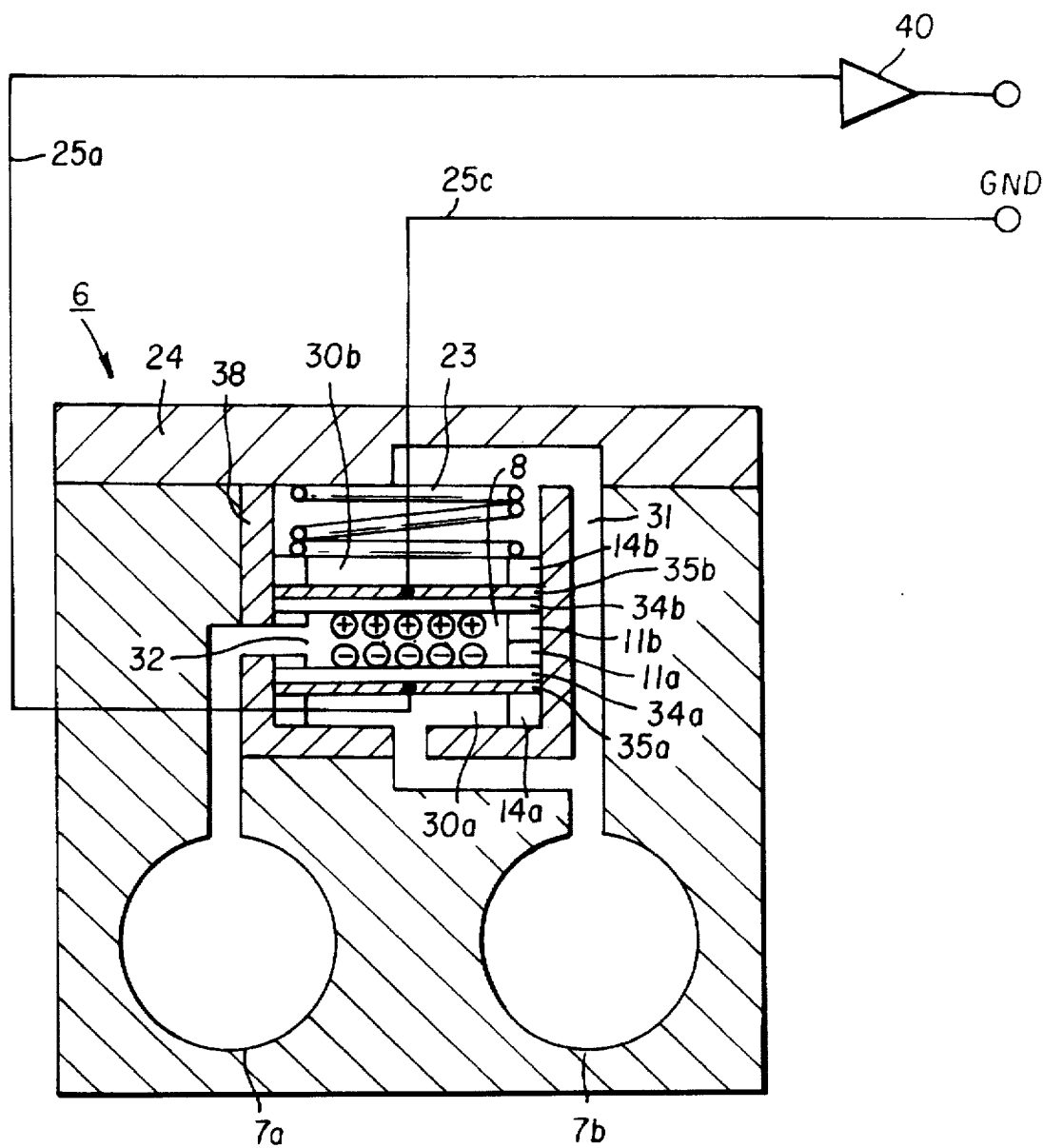
FIG. 6 is a view showing the structure of the fourth embodiment of the present invention.
Figure 7:
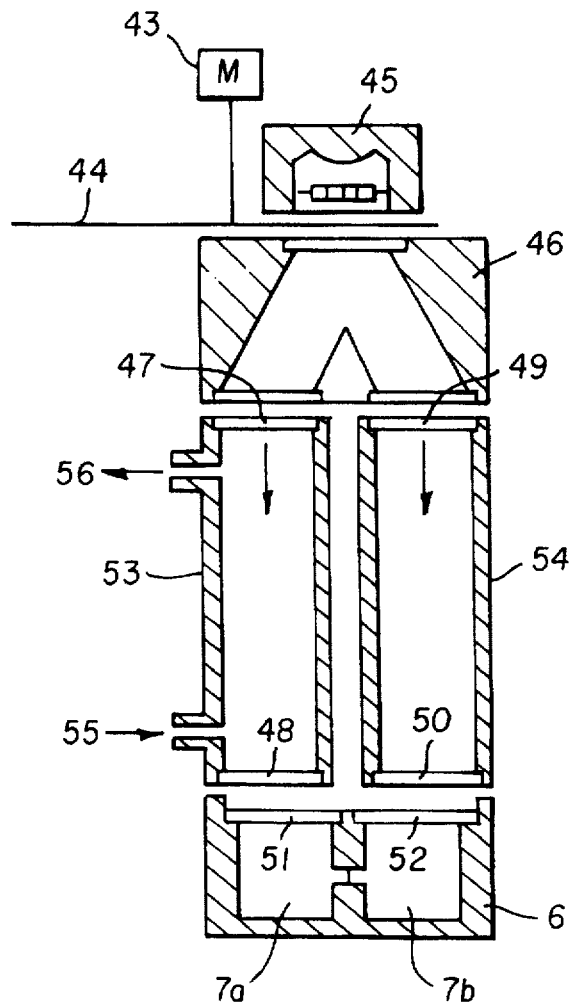
FIG. 7 is a view showing the whole structure of a known example of an infrared gas analyzer employing a pneumatic detector.
Figure 8:
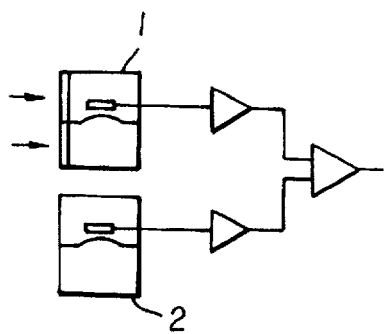
FIG. 8 is a view showing the structure of a first known example of a detector portion of the gas analyzer of FIG. 7.
Figure 9:
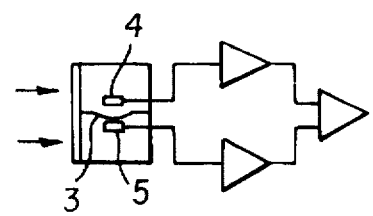
FIG. 9 is a view showing the structure of a second known example of a detector portion of the gas analyzer of FIG. 7.

FIG. 6 is a view showing the fourth embodiment of the present invention. This embodiment is different from that of FIGS. 4 and 5 in that the back plates 10a, 10b are eliminated, and that diaphragms 34a, 34b which consist of differently charged electret films are disposed in opposed relationship with each other, such that electrodes 35a, 35b each formed on one surface of the corresponding diaphragm 34a, 34b form a condenser. The voltage generated at the electrode 35a is received by a single amplifier 40, and the voltage generated at the electrode 35b is connected to the ground (GND).

In the above arrangement, when the pressure changes upon incidence of infrared rays, the diaphragms 34a, 34b are deformed in the opposite directions to produce pressure signals. If external vibrations are applied to the gas detector, on the other hand, the diaphragms 34a, 34b are deformed in the same direction, and generated signals are cancelled. It is thus possible to obtain outputs having high S/N ratios, even with a simple and inexpensive structure of the present embodiment.

What is claimed is:

1. A pneumatic infrared gas detector comprising:
first and second expansion chambers;
first and second pressure chambers, each of which is connected at one end thereof to a corresponding one of said first and second expansion chambers;
first and second diaphragms, respectively located in said first and second pressure chambers, for dividing each of said first and second pressure chambers into a first chamber connected to a corresponding one of the first and second expansion chambers and a second chamber, wherein said first chamber of said first pressure chamber is connected to said second chamber of said second pressure chamber through a first communication path, and wherein said second chamber of said first pressure chamber is connected to said first chamber of said second pressure chamber through a second communication path; and
first and second pneumatic pressure detecting elements, respectively located in said first and second pressure chambers, each of said first and second pneumatic pressure detecting elements comprising an electret film having one surface on which an electrode is formed and an electrode plate disposed in opposed relationship with said electret film, wherein said electret film is formed on a first side of a corresponding one of said first and second diaphragms in each of said first and second pressure chambers and said electrode plate is supported and fixed at a position that is opposed to a second side of said corresponding one of said first and second diaphragms.

2. A pneumatic infrared gas detector as defined in claim 1, wherein said first and second pressure chambers are disposed in parallel with each other on the same plane, and a single electret film, retained at opposite surface thereof, forms said first and second diaphragms in said first and second pressure chambers.

3. A pneumatic infrared gas detector comprising:
a pair of expansion chambers;
an upper pressure chamber and a lower pressure chamber connected to one of said pair of expansion chambers;
an intermediate pressure chamber formed between said upper pressure chamber and said lower pressure chamber, through upper and lower diaphragms, said intermediate pressure chamber being connected to the other of said pair of expansion chambers; and
an upper and a lower pneumatic pressure detecting element corresponding to said upper and lower diaphragms, each of which comprises an electret film having one surface on which an electrode is formed, and an electrode plate disposed in opposed relationship with said electret film, wherein said electret film of each of said upper and lower pneumatic pressure detecting elements is formed on a first side of a corresponding one of said upper and lower diaphragms and said electrode plate of each of said upper and lower pneumatic pressure detecting elements is supported and fixed at a position that is opposed to a second side of the corresponding one of said upper and lower diaphragms.

4. A pneumatic infrared gas detector comprising:
a pair of expansion chambers;
upper pressure chamber and lower pressure chamber connected to one of said pair of expansion chambers;
an intermediate pressure chamber formed between said upper pressure chamber and said lower pressure chamber, through respective upper and lower diaphragms, said intermediate pressure chamber being connected to the other of said pair of expansion chambers; and
upper and lower pneumatic pressure detecting elements, each including an electret film having one surface on which an electrode is formed, said electret films of said upper and lower pneumatic pressure detecting elements being charged to have different polarities;
wherein said upper and lower diaphragms respectively comprise said electret film of said upper and lower pressure detecting elements, which are positioned such that charged surfaces of the electret films of said upper and lower pressure detecting elements are opposed to each other.

5. A pneumatic infrared gas detector comprising:

first and second expansion chambers;

first and second pressure chambers, each of which is connected at one end thereof to a corresponding one of said first and second expansion chambers;

first and second diaphragms, respectively located in said first and second pressure chambers, for dividing each of said first and second pressure chambers into a first chamber connected to a corresponding one of said first and second expansion chambers and a second chamber, wherein said first chamber of said first pressure chamber is connected to said second chamber of said second pressure chamber through a first communication path, and wherein said second chamber of said first pressure chamber is connected to said first chamber of said second pressure chamber through a second communication path; and first and second pneumatic pressure detecting elements, respectively located in said first and second pressure chambers, each of said pneumatic pressure detecting elements comprising a back plate including an electret film and an electrode formed on a surface of the electret film;

wherein said first and second diaphragms are conductive and are provided so as to respectively face said first and second back plates.

6. A pneumatic infrared gas detector as defined in claim 5, wherein said first and second pressure chambers are disposed in parallel with each other on the same plane, and a single electret film, retained at opposite surface thereof, forms said first and second diaphragms in said first and second pressure chambers.

7. A pneumatic infrared gas detector comprising:

a pair of expansion chambers;

upper pressure chamber and lower pressure chamber connected to one of said pair of expansion chambers;

an intermediate pressure chamber formed between said upper pressure chamber and said lower pressure chamber, through upper and lower diaphragms, said intermediate pressure chamber being connected to the other of said pair of expansion chambers; and an upper and a lower pneumatic pressure detecting element corresponding to said upper and lower diaphragms, each of said pneumatic pressure detecting elements comprising a back plate including an electret film and the electrode formed on a surface of the electret film;

wherein said upper and lower diaphragms are conductive and are provided so as to respectively face said first and second back plates.

* * * * *